(12) United States Patent
Nicoson et al.

(10) Patent No.: US 8,442,623 B2
(45) Date of Patent: *May 14, 2013

(54) SITE MARKER VISIBLE UNDER MULTIPLE MODALITIES

(75) Inventors: Zachary R. Nicoson, Indianapolis, IN (US); Brian Zimmer, Indianapolis, IN (US); Joseph L. Mark, Indianapolis, IN (US); Nicholas Terwiske, Bloomington, IN (US); Laresha Fluker, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 209 days.

This patent is subject to a terminal disclaimer.

(21) Appl. No.: 12/133,212

(22) Filed: Jun. 4, 2008

(65) Prior Publication Data

US 2008/0269603 A1    Oct. 30, 2008

Related U.S. Application Data

(63) Continuation-in-part of application No. 11/242,334, filed on Oct. 3, 2005, now Pat. No. 8,280,486, which is a continuation-in-part of application No. 10/964,087, filed on Oct. 13, 2004, now abandoned.

(51) Int. Cl.
*A61B 6/00* (2006.01)
(52) U.S. Cl.
USPC .......................................................... 600/431
(58) Field of Classification Search .................... 600/431
See application file for complete search history.

(56) References Cited

U.S. PATENT DOCUMENTS

| 4,774,957 A | 10/1988 | Nambu et al. |
| 4,991,579 A | 2/1991 | Allen |
| 5,010,145 A | 4/1991 | Ikada et al. |
| 5,016,639 A | 5/1991 | Allen |
| 5,097,839 A | 3/1992 | Allen |
| 5,104,539 A | 4/1992 | Anderson et al. |
| 5,211,164 A | 5/1993 | Allen |
| 5,218,964 A | 6/1993 | Sepponen |
| 5,368,030 A | 11/1994 | Zinreich et al. |
| 5,397,329 A | 3/1995 | Allen |

(Continued)

FOREIGN PATENT DOCUMENTS

| EP | 1491147 | 12/2004 |
| EP | 1579878 | 9/2005 |

(Continued)

OTHER PUBLICATIONS

Final Office Action dated Feb. 16, 2010 for U.S. Appl. No. 10.964,087.

(Continued)

*Primary Examiner* — Unsu Jung
*Assistant Examiner* — Saurel J Selkin
(74) *Attorney, Agent, or Firm* — Vista IP Law Group LLP (57) ABSTRACT

Various embodiments of a site marker are disclosed that comprise a body portion and a marker element. The body portion is constructed of a bioabsorbable material and defines at least one cavity therein. The marker element is captured within one of the cavities. The marker element is constructed of a material that may be imaged under at least one imaging modality.

17 Claims, 6 Drawing Sheets

U.S. PATENT DOCUMENTS

| | | | |
|---|---|---|---|
| 5,427,099 A | 6/1995 | Adams | |
| 5,469,847 A | 11/1995 | Zinreich et al. | |
| 5,693,085 A | 12/1997 | Buirge et al. | |
| 5,730,130 A * | 3/1998 | Fitzpatrick et al. | 600/407 |
| 5,769,789 A | 6/1998 | Wang et al. | |
| 5,782,764 A | 7/1998 | Werne | |
| 5,902,310 A | 5/1999 | Foerster et al. | |
| 5,941,890 A | 8/1999 | Voegele et al. | |
| 5,961,455 A | 10/1999 | Daum et al. | |
| 6,011,987 A | 1/2000 | Barnett | |
| 6,015,844 A | 1/2000 | Harvey et al. | |
| 6,016,439 A | 1/2000 | Acker | |
| 6,056,700 A | 5/2000 | Burney et al. | |
| 6,057,700 A | 5/2000 | Crispell | |
| 6,173,715 B1 | 1/2001 | Sinanan et al. | |
| 6,228,055 B1 | 5/2001 | Foerster et al. | |
| 6,231,834 B1 | 5/2001 | Unger et al. | |
| 6,261,302 B1 | 7/2001 | Voegele et al. | |
| 6,270,464 B1 | 8/2001 | Fulton, III et al. | |
| 6,280,385 B1 | 8/2001 | Melzer et al. | |
| 6,333,971 B2 | 12/2001 | McCrory et al. | |
| 6,347,241 B2 * | 2/2002 | Burbank et al. | 600/431 |
| 6,350,244 B1 * | 2/2002 | Fisher | 600/562 |
| 6,356,782 B1 | 3/2002 | Sirimanne et al. | |
| 6,371,904 B1 * | 4/2002 | Sirimanne et al. | 600/3 |
| 6,379,379 B1 | 4/2002 | Wang | |
| 6,427,081 B1 | 7/2002 | Burbank et al. | |
| 6,466,813 B1 | 10/2002 | Shukla et al. | |
| 6,544,185 B2 | 4/2003 | Montegrande | |
| 6,567,687 B2 | 5/2003 | Front et al. | |
| 6,628,982 B1 | 9/2003 | Thomas et al. | |
| 6,640,127 B1 | 10/2003 | Kosaka et al. | |
| 6,687,533 B1 | 2/2004 | Hirano et al. | |
| 6,699,205 B2 | 3/2004 | Fulton, III et al. | |
| 6,725,083 B1 | 4/2004 | Burbank et al. | |
| 6,766,186 B1 | 7/2004 | Hoyns et al. | |
| 6,862,470 B2 | 3/2005 | Burbank et al. | |
| 7,229,417 B2 | 6/2007 | Foerster et al. | |
| 7,611,462 B2 | 11/2009 | Vortman et al. | |
| 7,625,397 B2 | 12/2009 | Foerster et al. | |
| 2001/0049549 A1 | 12/2001 | Boylan et al. | |
| 2002/0035324 A1 * | 3/2002 | Sirimanne et al. | 600/431 |
| 2002/0082517 A1 | 6/2002 | Klein | |
| 2002/0156372 A1 | 10/2002 | Skakoon et al. | |
| 2002/0161298 A1 | 10/2002 | Burbank et al. | |
| 2002/0188196 A1 | 12/2002 | Burbank et al. | |
| 2002/0193815 A1 | 12/2002 | Foerster et al. | |
| 2003/0004563 A1 | 1/2003 | Jackson et al. | |
| 2003/0097059 A1 | 5/2003 | Sorrell et al. | |
| 2003/0139669 A1 | 7/2003 | Montegrande | |
| 2003/0199785 A1 | 10/2003 | Hibner et al. | |
| 2004/0030237 A1 | 2/2004 | Lee et al. | |
| 2004/0030262 A1 | 2/2004 | Fisher et al. | |
| 2004/0049224 A1 | 3/2004 | Buehlmann et al. | |
| 2004/0093069 A1 * | 5/2004 | Priewe et al. | 623/1.15 |
| 2004/0097981 A1 | 5/2004 | Selis | |
| 2004/0105890 A1 | 6/2004 | Klein et al. | |
| 2004/0110059 A1 | 6/2004 | Onishi et al. | |
| 2004/0116802 A1 | 6/2004 | Jessop et al. | |
| 2004/0116805 A1 | 6/2004 | Chesbrough et al. | |
| 2004/0116806 A1 | 6/2004 | Burbank et al. | |
| 2004/0138555 A1 | 7/2004 | Krag et al. | |
| 2004/0219186 A1 * | 11/2004 | Ayres | 424/426 |
| 2005/0033157 A1 | 2/2005 | Klein et al. | |
| 2005/0063908 A1 | 3/2005 | Burbank et al. | |
| 2005/0277871 A1 | 12/2005 | Selis | |
| 2005/0288764 A1 | 12/2005 | Snow et al. | |
| 2006/0009712 A1 | 1/2006 | Van Bladel et al. | |
| 2006/0079805 A1 | 4/2006 | Miller et al. | |
| 2006/0173296 A1 | 8/2006 | Miller et al. | |
| 2007/0093726 A1 | 4/2007 | Leopold et al. | |
| 2007/0118176 A1 | 5/2007 | Opolski et al. | |
| 2007/0167980 A1 | 7/2007 | Figulla et al. | |
| 2008/0058715 A1 | 3/2008 | Houser et al. | |
| 2008/0269603 A1 | 10/2008 | Nicoson | |

FOREIGN PATENT DOCUMENTS

| | | |
|---|---|---|
| EP | 1 602 341 A1 | 12/2005 |
| EP | 1 925 266 A2 | 5/2008 |
| WO | WO-0024332 | 5/2000 |
| WO | WO-01/00101 A1 | 1/2001 |
| WO | WO-01/08578 A1 | 2/2001 |
| WO | WO-0230482 | 4/2002 |
| WO | WO-2004/012600 | 2/2004 |

OTHER PUBLICATIONS

Response to Final Office Action dated Feb. 16, 2010 for U.S. Appl. No. 10/964,087.
ACS Industries, Inc. publication entitled "ImagineKnit, We'll Provide It!" Sep. 2003.
Alatassi, Houda et al., "Breast Biopsy Marker Masquerading as a Mass Lesion", The Breast Journal, vol. 11, Nov. 6, 2006, pp. 504-505.
Wahner-Roedler, Dietlind L., "Vacuum-Assisted Breast Biopsy Device (Mammotome) Malfunction Simulating Microcalcifications", The Breast Journal, vol. 11, Nov. 6, 2005, pp. 474-475.
PCT International Search Report for PCT/US2005/034809.
PCT International Search Report #PCT/IB2006/053546.
Office Action dated Aug. 4, 2009 for U.S. Appl. No. 10/964,087.
Response to Office Action dated Aug. 4, 2009 for U.S. Appl. No. 10/964,087.
PCT International Search Report for PCT/US2009/046200 dated Oct. 5, 2009.
Non-Final Office Action dated Jun. 8, 2010 for U.S. Appl. No. 10/964,087.
Amendment After Final Office Action filed with RCE in response to Advisory Action dated May 6, 2010 for U.S. Appl. No. 10/964,087.
Non-Final Office Action dated Aug. 4, 2010 for U.S. Appl. No. 12/269,501.
Non-Final Office Action dated Jun. 28, 2010 for U.S. Appl. No. 11/242,334.
Response to Non-Final Office Action dated Jun. 8, 2010 for U.S. Appl. No. 10/964,087.
Response to Non-Final Office Action dated Jun. 28, 2010 for U.S. Appl. No. 11/242,334.
Response to Non-Final Office Action dated Aug. 4, 2010 for U.S. Appl. No. 12/269,501.
Annex to the European Search Report dated Aug. 18, 2010 for EP07254526.
Non-Final Office Action dated Dec. 8, 2010 in U.S. Appl. No. 10/964,087.
Final Office Action dated Jan. 4, 2011 for U.S. Appl. No. 11/242,334.
Non-Final Office Action dated Dec. 27, 2010 for U.S. Appl. No. 11/561,919.
Non-Final Office Action dated Feb. 17, 2011 for U.S. Appl. No. 12/269,501.
Response to Non-Final Office Action dated Dec. 8, 2010 for U.S. Appl. No. 10/964,087.
Response to Non-Final Office Action dated Dec. 27, 2010 for U.S. Appl. No. 11/561,919.
Response to Final Office Action dated Jan. 4, 2011 for U.S. Appl. No. 11/242,334.
Final Office Action dated May 19, 2011 for U.S. Appl. No. 10/964,087.
Notice of Allowance dated Jun. 10, 2011 for U.S. Appl. No. 11/561,919.
Non-Final Office Action dated Jul. 6, 2011 for U.S. Appl. No. 11/242,334.
Final Office Action dated Aug. 3, 2011 for U.S. Appl. No. 12/269,501.
Response to Non-Final Office Action dated Jul. 6, 2011 for U.S. Appl. No. 11/242,334.

* cited by examiner

SITE MARKER VISIBLE UNDER MULTIPLE MODALITIES

CROSS REFERENCE TO RELATED APPLICATIONS

This application is a Continuation-in-part of U.S. application Ser. No. 11/242,334, filed Oct. 3, 2005, which application is a continuation-in-part of U.S. Ser. No. 10/964,087, entitled SITE MARKER VISIBLE UNDER MULTIPLE MODALITIES, filed Oct. 13, 2004, both applications of which are incorporated herein in their entirety.

TECHNICAL FIELD

The present disclosure relates generally to site markers for breast biopsy procedures.

BACKGROUND

In the diagnosis and treatment of breast cancer, it is often necessary to perform a biopsy to remove tissue samples from a suspicious mass. The suspicious mass is typically discovered during a preliminary examination involving visual examination, palpation, X-ray, magnetic resonance imaging (MRI), ultrasound imaging or other detection means.

When a suspicious mass is detected, a sample is taken by biopsy, and then tested to determine whether the mass is malignant or benign. This biopsy procedure can be performed by an open surgical technique, or through the use of a specialized biopsy instrument. To minimize surgical intrusion, a small specialized instrument such as a biopsy needle is inserted in the breast while the position of the needle is monitored using fluoroscopy, ultrasonic imaging, X-rays, MRI or other suitable imaging techniques.

In one biopsy procedure, referred to as stereotactic needle biopsy, the patient lies on a special biopsy table with her breast compressed between the plates of a mammography apparatus and two separate X-rays are taken from two different points of reference. A computer then calculates the exact position of the mass or lesion within the breast. The coordinates of the lesion are then programmed into a mechanical stereotactic apparatus which advances the biopsy needle into the lesion with precision. At least five biopsy samples are usually taken from locations around the lesion and one from the center of the lesion.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, and the original features of the tissue may have been removed or altered by the biopsy, it is desirable to insert a site marker into the surgical cavity to serve as a landmark for future identification of the location of the lesion.

Known biopsy site markers have been found to have disadvantages in that the site markers are not visible under all available modalities. Moreover, because of this problem, when cancer is found at a biopsy site that has been previously marked with a site marker, due to the poor visibility of the biopsy site marker under ultrasound or other visualization modalities, the patient must undergo an additional procedure that places an additional device within the biopsy site to enable the surgeon to find the biopsy site in subsequent procedures. One known technique has been to place a breast lesion localization wire at the biopsy site. The localization wire is typically placed at the biopsy site via mammography and/or ultrasound.

Another issue that arises with site markers is migration. When the site markers are typically deployed to the biopsy site, the breast is still under compression. However, when the breast is released from compression, the site marker may migrate within the site or even out of the site through a needle tract created by the biopsy device, thereby preventing a surgeon or radiologist from easily locating the precise location of the lesion or biopsied area.

Accordingly, there is a need for site markers made from biocompatible materials that are visible under various modes of imaging to reduce the number of procedures that patients must undergo in detection and treatment of cancer. There is also a need to limit migration of a site marker when the site marker is placed in a biopsy site.

SUMMARY

A site marker is disclosed comprising a body portion and a marker element. The body portion is constructed of a bioabsorbable material and defines at least one cavity therein. The marker element is captured within one of the cavities. The marker element is constructed of a material that may be imaged under at least one imaging modality.

BRIEF DESCRIPTION OF THE DRAWINGS

These and other features and advantages of the invention will be apparent from the following detailed description and the appended claims, taken in conjunction with the accompanying drawings, in which:

DETAILED DESCRIPTION

Figure 1:
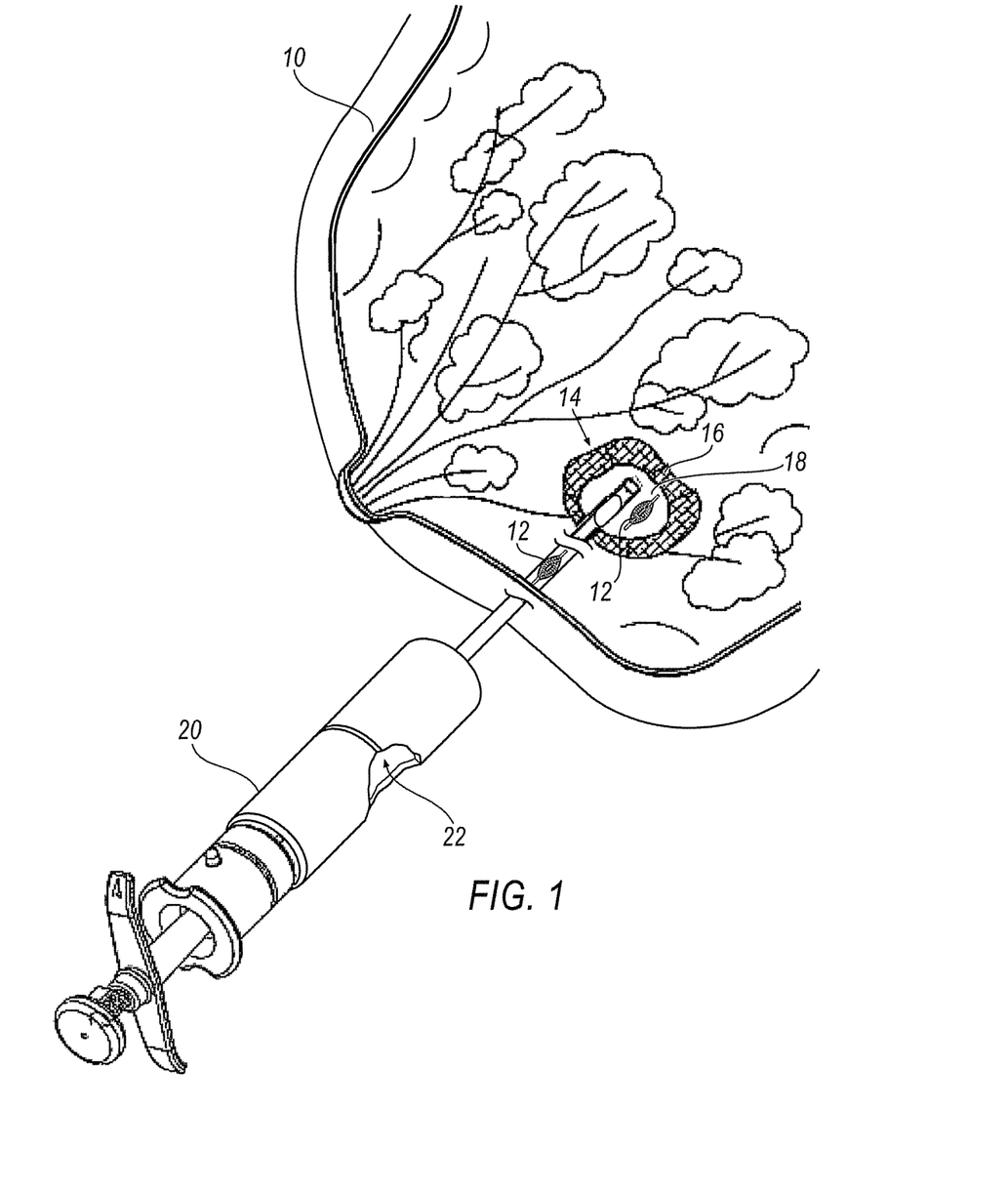
FIG. 1 is a perspective view of a biopsy site in a human breast showing the breast in section and one or more site markers being implanted in the biopsy cavity using a site marker delivery system.

FIG. 1 illustrates a perspective view of a human breast 10 being implanted with a site marker 12 according an embodiment of the disclosure. At a biopsy site 14 is a lesion 16 from which a tissue sample has been removed, resulting in a biopsy cavity 18. One or more site markers 12 are implanted in the biopsy cavity 18 using a marker delivery system 20, as shown in FIG. 1. In one embodiment, the marker delivery system 20 is slidably advanced through an inner lumen 22 of a biopsy device (not shown), which avoids the need to withdraw the biopsy device and thereafter insert the marker delivery system 20. Delivering the site marker 12 in the biopsy cavity 18 without withdrawing the biopsy device reduces the amount of tissue damage and enables more accurate placement of the site marker 12. The marker delivery system 20 illustrated in FIG. 1 is exemplary only and it is understood that the site marker embodiments disclosed herein are suitable for use with other marker delivery systems.

FIGS. 2-9 illustrate various exemplary site marker embodiments according to the present disclosure. In general, the site markers described herein are made, at least in part, from biocompatible materials such as, but not limited to, titanium, stainless steel, and platinum. These materials have appropriate densities for radiographic imaging, appropriate surface characteristics for ultrasonic imaging, and appropriate magnetic characteristics for magnetic resonance imaging.

Figure 2:
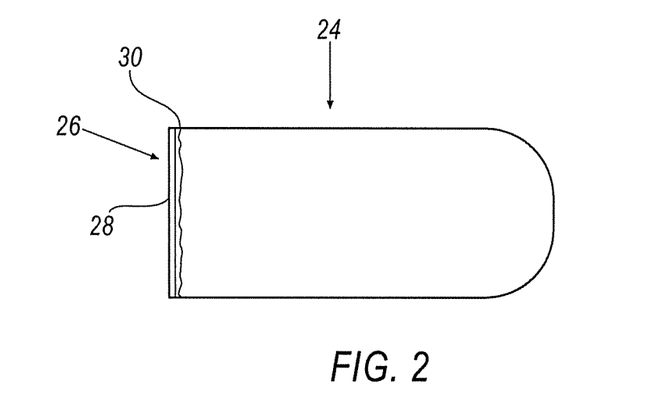
FIG. 2 is a side elevational view of an embodiment of a site marker.

Referring initially to FIG. 2, a hollow site marker in the form of a capsule 24 having an open end 26 is illustrated. A cap 28 is attached to the open end 26 by a suitable method, such as a weld 30 or a surgical adhesive. In one embodiment, capsule is constructed of a bioabsorbable material, which may also be visible under one or more imaging modalities.

Figure 2A:
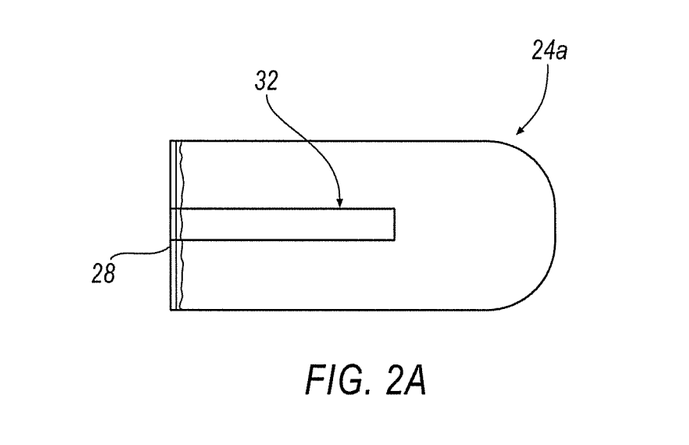
FIG. 2A is a side elevational view of another embodiment of a site marker.

In another embodiment, the capsule 24 is constructed of a material that is designed to resonate at a predetermined ultrasound frequency. The resonance will be visible under one or more imaging modalities. In the event that the capsule 24 needs to resonate at more than one frequency, a resonant beam 32, as shown in FIG. 2A, can be attached to an inner surface wall of the cap 28 so that the beam resonance is transmitted through the wall of the capsule 24a. The capsule 24 may be constructed from any biocompatible material with suitable echogenic properties such as, but not limited to, titanium, stainless steel, or platinum.

Figure 3A:
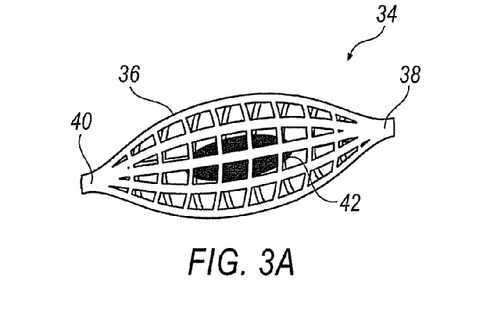
FIG. 3A is a side elevational view of another embodiment of a site marker.

Referring to FIG. 3A, another embodiment of a site marker 34 is shown. Site marker 34 includes a generally hollow body portion 36 that is flanked by closed ends 38, 40. Positioned within body portion 36 is a smaller permanent marker 42 that is captured therein. However, permanent marker 42 need not be attached to body portion 36 in any way. Permanent marker 42 is preferably constructed of a suitable material that will not biodegrade within the body and which may be viewed under multiple imaging modalities, such as Magnetic Resonance Imaging (MRI). Examples of suitable materials for permanent marker 88 include, but are not limited to, titanium, stainless steel, ceramic, carbon, nickel titanium, and glass. Permanent marker 42 may be any provided in any shape. In one embodiment, permanent marker 42 has a predefined shape, as shown, for example, in FIGS. 5, 8 and 9B.

In one embodiment, body portion 36 is constructed of a bioabsorbable material such as polyglycolic acid (PGA), polylactic acid (PLA), hydrogel, collegen-based material or any other suitable material. The bioabsorbable material may be woven into a flexible mesh that has openings formed therein that are sized so as to be smaller than permanent marker 42 such that permanent marker 42 cannot escape body portion 36. After installation in a biopsy cavity, over a predetermined time period, such as, for example, a few weeks to several months, body portion 36 is absorbed by the body, such that only permanent marker 42 remains within the body at the biopsy cavity. Because permanent marker 42 is captured within body portion 36 prior to absorption thereof by the body, permanent marker 42 is restricted from migrating from within the biopsy cavity. Indeed, movement of permanent marker 42 is limited to the internal cavity defined by body portion 36. This insures that permanent marker 42 remains within the biopsy cavity to permit follow-up imaging of the biopsy site.

Figure 3B:
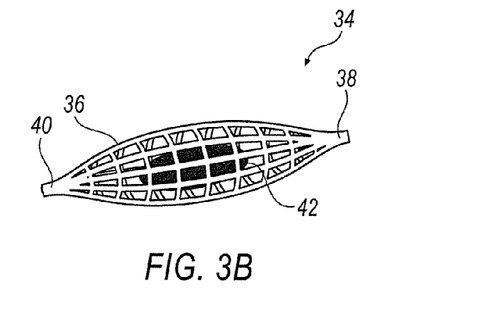
FIG. 3B is a side elevational view of the site marker of FIG. 3A in a pre-deployment configuration.

In one embodiment, prior to deployment into the biopsy site by a suitable deployment mechanism, site marker 34, and more specifically, body portion 36, is formed in a first pre-deployment configuration (as shown in FIG. 3B), whereby the site marker 34 is compressed into a predetermined size and shape so as to be readily positionable within the deployment device. In fact, site marker 34 may be positioned in the deployment device prior to shipping deployment device. Once site marker 34 exits the deployment device into the biopsy site, site marker 34 is released from its compressed first pre-deployment configuration and automatically expands into a second post-deployment configuration (shown in FIG. 3A), whereby at least a portion of the body portion 36 of the site marker 34 expands at least as much as the outside diameter of the deployment device to form a close cage that holds permanent marker 42 such that site marker 34 cannot migrate back into the deployment device.

Figure 3C:
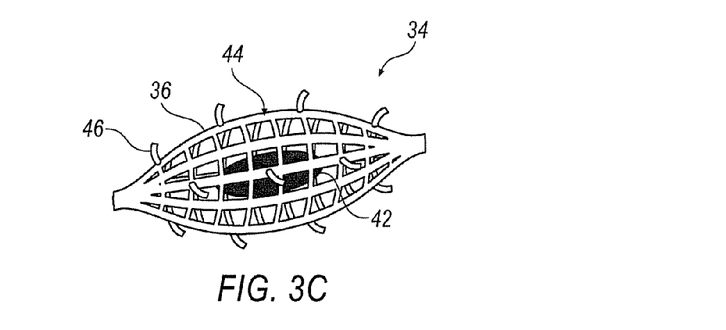
FIG. 3C is a side elevational view of another embodiment of a site marker.

In another embodiment, as shown in FIG. 3C, an outside surface 44 of body portion 36 is provided with one or more barbs 46 disposed thereon. The barbs 46 assist in adhering site marker 34 to internal walls of the biopsy cavity. Barbs 46 are configured so as to extend at a predetermined angle relative to outside surface 44. In one specific embodiment, barbs 46 are configured to extend perpendicular to outside surface 44. In another embodiment, barbs 46 are positioned at different angles relative to one another, including opposing one another.

Figure 3D:
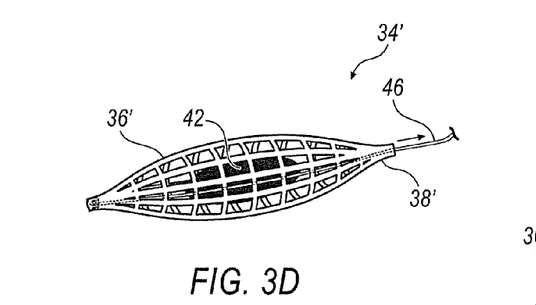
FIG. 3D is a side elevational view of an embodiment of a site marker in a pre-deployment position.
Figure 3E:
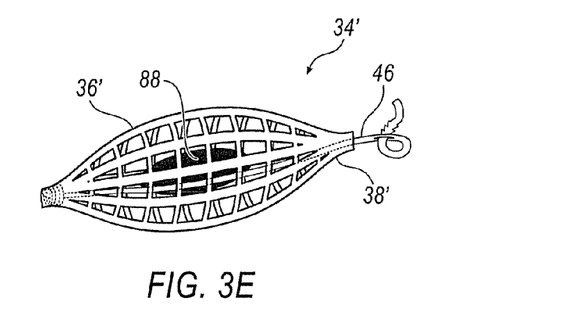
FIG. 3E is a side elevational view of the site marker of FIG. 3D in a post-deployment position.

In another embodiment, as shown in FIGS. 3D and 3E, body portion 36' of site marker 34' is manually expanded from a first pre-deployment configuration (FIG. 3D) into a second post-deployment configuration (FIG. 3E). In this embodiment, site marker 34' is provided with a thread 46 or deployment line (e.g., thread, filament, wire) that is attached to the forward end 38' of body portion 36'. In one embodiment, thread 46 is held by a tie-wrap style clinch via the deployment device. Once the site marker 34' is deployed, the tie-wrap pulls on thread 46 which pops open body portion 36' to the second post-deployment device to a predetermined maximum size. Upon reaching the predetermined maximum size, the deployment device severs thread 46, releasing site marker 34' into the biopsy site.

Figure 4A:
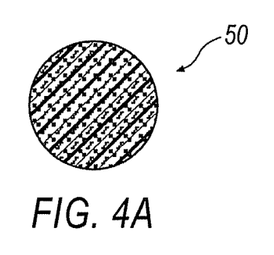
FIG. 4A is an end view of another embodiment of a site marker.
Figure 4B:
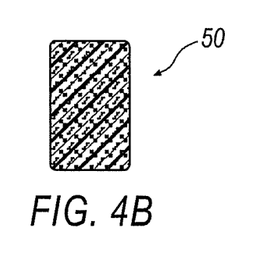
FIG. 4B is an end view of the site marker of FIG. 4A in a pre-deployment configuration.
Figure 4C:
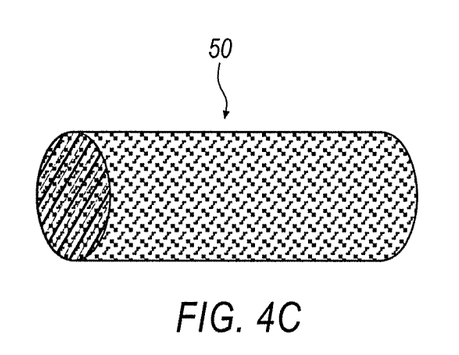
FIG. 4C is a side elevational view of the site marker of FIG. 4A in a post-deployment configuration.

FIG. 4A-4C depict a site marker 50 that is constructed of a foam-like material. The foam-like material may be a carbon filled polymer or a glass filled polymer so as to be visible under multiple modalities. In addition, the foam-like material may contain therapeutic materials to deliver medication to the biopsy site. One exemplary material for construction of site marker 50 is a thrombin filled polymer. The foam-like material acts as a matrix for tissue ingrowth.

Site marker 50 expands from a first pre-deployment configuration (shown in FIG. 4B) to a second post-deployment configuration (shown in FIG. 4C). In the first pre-deployment configuration, site marker is substantially compressed in either length or width or both so as to be receivable within a suitable deployment device. The site marker may remain in the pre-deployment device for an extended period of time, such that it may be desirable to pre-load a deployment device with one or more of the site markers in the first pre-deployment configuration.

In one embodiment, the material may from which site marker 50 is constructed is a shape memory material that will spring into the second post deployment configuration upon release from a deployment device into a biopsy cavity. In accordance with this embodiment, the site marker is designed to have a predetermined shape and then compressed into the first pre-deployment configuration. The site marker is then retained in the first pre-deployment configuration and may be loaded into a deployment device. It should be noted that the site marker may be stored in the deployment device in the first pre-deployment configuration for an extended period of time.

Once released from the deployment device and into the biopsy cavity, the site marker automatically springs into the second post-deployment configuration having a predetermined size and shape such that the site marker is easily visible under various imaging modalities.

In another embodiment, site marker 50 is constructed of a temperature dependent material. In accordance with this embodiment, the site marker does not expand from the first pre-deployment configuration into the second post-deployment configuration until heat is applied to the site marker 50. Deploying the site marker 50 into a biopsy cavity provides a sufficient level of heat generated from the body to enable site marker 50 to automatically expand into the second post-deployment configuration after deployment.

Figure 5:
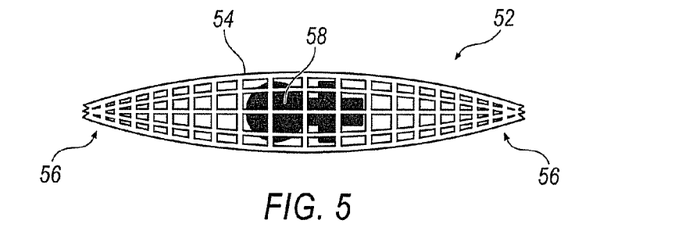
FIG. 5 is a side elevational view of another embodiment of a site marker.

Another embodiment of a site marker 52 is shown in FIG. 5. Site marker 52 includes a body portion 54, similar to body portion 36. In one embodiment, body portion 54 is constructed of a tube of bioabsorbable material, having open ends. The ends 56 are stitched or weaved, to cinch each end 56, thereby minimizing the size of a cavity defined by body portion 54 so as to create a cavity that is as small as possible for retaining a permanent marker 58.

While body portion 54 is illustrated as a mesh material having small openings therethrough, it is understood that the embodiment is not limited to use of a mesh material. Indeed, the material need not have any small openings therein. Further, in the embodiment shown in FIG. 5, body portion 54 can, but need not expand once deployed from a site marker deployment device and positioned within the biopsy cavity.

As mentioned above, the permanent marker 58 may be any shape. To facilitate its recognition, permanent marker 58 may (but is not required to) have a predefined shape, such as the Venus symbol as shown in FIG. 5, the bow-tie symbol shown in FIG. 8, or the ribbon symbol shown in FIGS. 9A and 9B.

Figure 6:
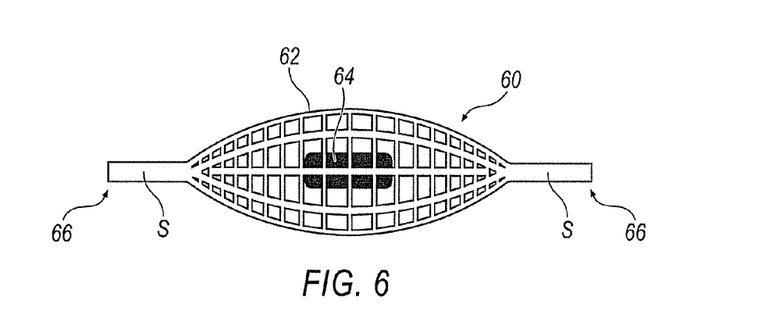
FIG. 6 is a side elevational view of another embodiment of a site marker.

FIG. 6 illustrates another alternative embodiment of a site marker 60. Site marker 60 comprises a body portion 62 and a permanent marker 64. Body portion 62 is constructed of a bioabsorbable material and defines a cavity in which permanent marker 64 is housed. To minimize the size of the cavity, a segment S of body portion 62 adjacent to each end 66 is secured together, such as by fusing or other suitable methods. Indeed, by securing the segments S together, the cavity may be minimized so as to further restrict movement of the permanent marker 64, especially once deployed within the biopsy site. Thus, migration of the permanent marker 64 is minimized.

Figure 7:
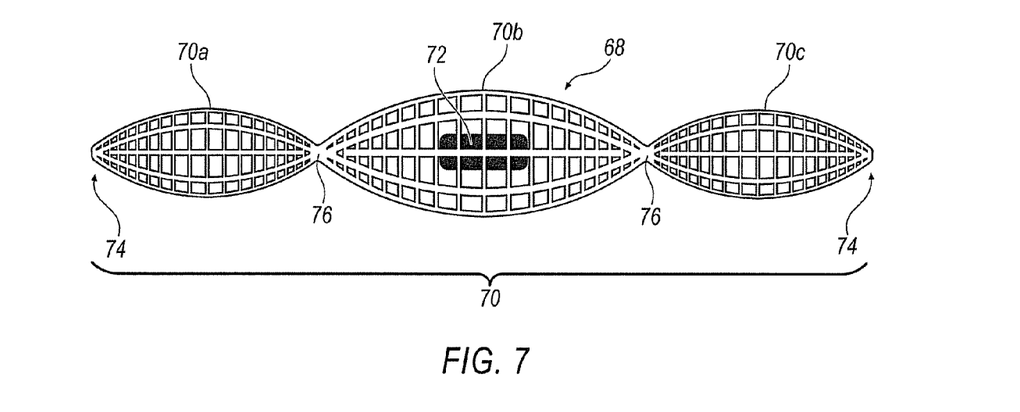
FIG. 7 is side elevational view of another embodiment of a site marker.

Another embodiment of a site marker 68 is shown in FIG. 7. In this embodiment, site marker 68 includes a body portion 70 and a permanent marker 72. Body portion 70 is constructed of a bioabsorbable material and flanked by two ends 74 that are closed. However, body portion 70 is also attached or fused at least at one additional location 76. In the specific, exemplary embodiment shown in FIG. 7, body portion 70 is fused at two additional locations 76. By fusing together at least one location of body portion 70 and spaced from one of the ends 74, separate cavities 70A, 70B, and 70C, may be created. In one of those cavities 70B, permanent marker 72 is positioned. Because body portion 70 is segmented to form the separate cavities, a smaller cavity 70B may be formed (as compared to a cavity simply defined by body portion 70 and ends 74) into which permanent marker 72 is placed. By minimizing the cavity 70B size, movement of the permanent marker 72 is restricted. Thus, when deployed into a biopsy cavity, migration of the permanent marker 72 will also be minimized.

While the embodiment shown in FIG. 7 illustrates one permanent marker 72 disposed in a center cavity 70B, it is understood that the marker 72 may be disposed in any of the cavities. Indeed, each cavity may be provided with its own permanent marker 72. In yet another embodiment, one or more of the cavities may be provided with a therapeutic agent or a haemostatic agent, as well. Further, while the exemplary embodiment shown in FIG. 7 illustrates the fusing or attachment locations 76 be to generally spaced apart in an equidistantly, it is also understood the fusing or attachment locations 76 may be positioned at a variety of intervals and may also includes more than two locations.

While body portion 70 is illustrated as a mesh material having small openings therethrough, it is understood that the embodiment is not limited to use of a mesh material. Indeed, the material need not have any small openings therein. Further, in the embodiment shown in FIG. 7, body portion 70 can, but need not expand once deployed from a site marker deployment device and positioned within the biopsy cavity.

Figure 8:
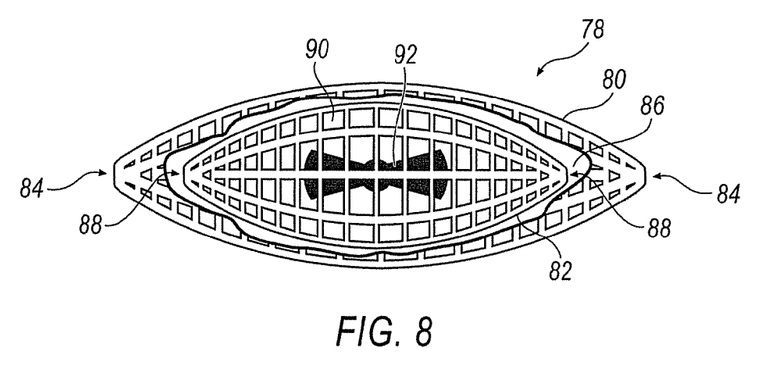
FIG. 8 is side elevational view of another embodiment of a site marker.

Another embodiment of a site marker 78 is illustrated in FIG. 8. Site marker 78 comprises a first body portion 80 and a second body portion 82, both of which are constructed of a bioabsorbable material. First body portion 80 is defined by two ends 84 that are closed off and cooperate to define a first cavity 86 within first body portion 80. Second body portion 82 is positioned within first cavity 86. Accordingly, second body portion 82 is at least slightly smaller than first cavity 86 of first body portion 80. Second body portion 82 is defined by two ends 88 that are closed off and cooperate to define a second cavity 90. Disposed within second cavity 90 is a permanent marker 92.

Due to the nested configuration of first and second body portions 80 and 82 and permanent marker 92, movement of the permanent marker 92 will is restricted to second cavity 90. Thus, when deployed into a biopsy cavity, migration of the permanent marker 92 will be minimized.

While body portion 70 is illustrated as a mesh material having small openings therethrough, it is understood that the embodiment is not limited to use of a mesh material. Indeed, the material need not have any small openings therein. Further, in the embodiment shown in FIG. 7, body portion 70 can, but need not expand once deployed from a site marker deployment device and positioned within the biopsy cavity.

Figure 9A:
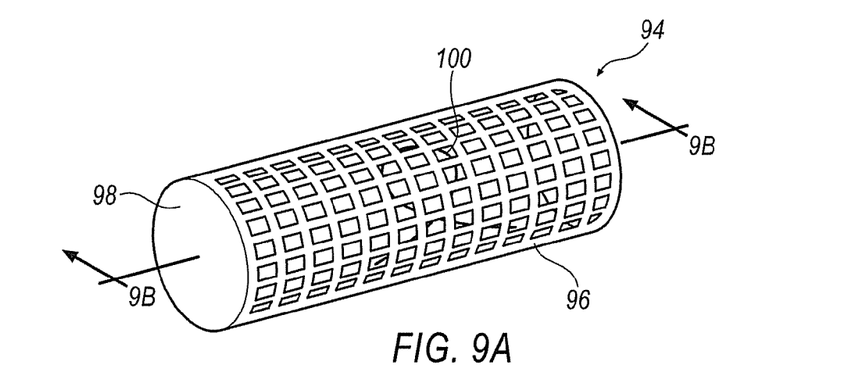
FIG. 9A is a perspective view of another embodiment of a site marker.
Figure 9B:
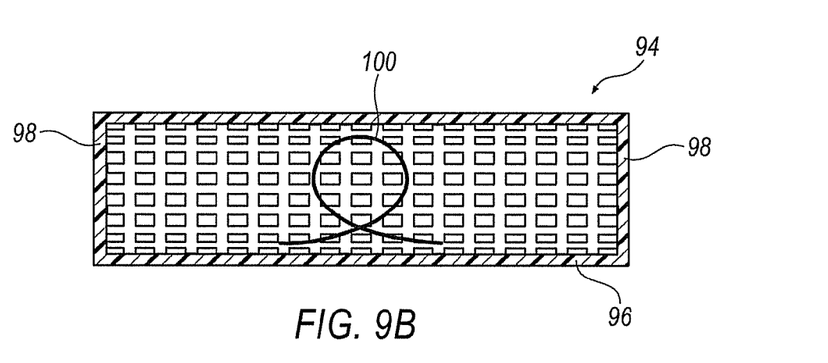
FIG. 9B is a cross-sectional view of the site marker of FIG. 9A taken along lines 9B-9B.

FIGS. 9A-9B illustrate yet another embodiment of a site marker 94. Site marker 94 comprises includes a generally hollow cannula body 96 constructed of a bioabsorbable material. Ends 98 of cannula body 96 are at least partially sealed (or may be fully sealed) to create a chamber within the body 96. A permanent marker 100 component is housed in the chamber within the cannula body 86 and allowed to free-float within the cannula body 96. By at least partially sealing the ends 98 of the cannula body 96, permanent marker 100 remains trapped within the chamber of the cannula body 96. Site marker 94 is constructed to fill a substantial space within a biopsy cavity, but still at least minimize migration of the permanent marker 100 as the permanent marker 100 is trapped within the cannula body 96.

In one embodiment, cannula body 96 is illustrated as a mesh having a plurality of openings that are substantially smaller than the size of the permanent marker 100. Thus, permanent marker 100 is prevented from escaping from the chamber of the cannula body 96 when the ends 98 are sealed. It is also understood, however, that the cannula body 96 may be constructed of a bioabsorbable material that does not have any openings without departing from the disclosure.

While the present invention has been particularly shown and described with reference to the foregoing preferred embodiments, it should be understood by those skilled in the art that various alternatives to the embodiments of the invention described herein may be employed in practicing the invention without departing from the spirit and scope of the invention as defined in the following claims. It is intended that the following claims define the scope of the invention embodiments within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiment is illustrative, and no single feature or element is essential to all possible combinations that may be claimed in this or a later application.

What is claimed is:

1. A site marker comprising:
a first body portion that defines a first cavity therein;
a second body portion that defines a second cavity therein; and wherein the second body portion is positioned within the first cavity; and
at least one imageable marker element captured within the second cavity such that the imageable marker element is moveable within the second cavity,
wherein the material of the second body portion is a flexible mesh material having openings therein, and
wherein said openings are smaller in size than the size of the marker element such that the marker element cannot escape the second cavity.

2. A site marker comprising:
a first body portion that defines a first cavity therein;
a second body portion that defines a second cavity therein; and wherein the second body portion is positioned within the first cavity; and
at least one imageable marker element captured within the second cavity such that the imageable marker element is moveable within the second cavity,
wherein the marker element has a predetermined shape based on visibility of the marker element under a certain imaging modality, and
wherein the predetermined shape is one of a Venus symbol, bow-tie, and ribbon.

3. A site marker, comprising:
a body portion, wherein the body portion is flanked by at least partially closed ends and wherein the body portion is attached to itself at a first location that is spaced inwardly from one of the ends such that the partially closed ends cooperate with the first location so as to create more than one cavity; and
at least one imageable marker element captured within at least one of the more than one cavities, but enabling the marker to move within the cavity.

4. The site marker of claim 3, wherein the body portion is formed as a hollow cannula.

5. The site marker of claim 3, wherein the body portion is attached to itself at a second location that is spaced inwardly from the ends of the body portion.

6. The site marker of claim 3, wherein each cavity houses a separate marker element.

7. A site marker, comprising:
a body portion that defines at least one cavity of open space therein; and
at least one imageable solid marker element wherein the imageable solid marker element is captured within the at least one cavity, such that said imageable solid marker element is permitted to move freely within the entire open space of the at least one cavity.

8. The site marker of claim 7, wherein the body portion is flanked by at least partially closed ends.

9. The site marker of claim 8, wherein the partially closed ends are closed to a degree prevents the imageable solid marker from escaping the cavity.

10. The site marker of claim 7, comprising a first fused segment and a second fused segment, with the cavity being positioned between the first and second fused segments.

11. The site marker of claim 7, wherein the body portion is defined by a first end and a second end, and wherein the first and second ends of the body portion are woven so as to close the body portion to form the cavity.

12. The site marker of claim 7, wherein the body portion defines a plurality of cavities and wherein one of the cavities includes a therapeutic agent.

13. The site marker of claim 7, wherein the body portion is constructed with openings therein, wherein said openings are smaller in size than the size of the imageable solid marker element such that the imageable solid marker element cannot escape the cavity.

14. The site marker of claim 7, wherein the imageable solid marker element is a three dimensional imageable marker element.

15. The site marker of claim 7, wherein the imageable solid marker element is permitted to move freely within the entire open space of the at least one cavity without being impeded by any other material.

16. The site marker of claim 7, wherein the imageable solid marker element comprises foam.

17. A site marker, comprising:
a body portion that defines at least one cavity of open space therein; and
at least one imageable solid marker element, wherein the imageable solid marker element is captured within the at least one cavity, such that said imageable solid marker element is permitted to move freely within the cavity, wherein the body portion defines a plurality of cavities and wherein one of the cavities includes a therapeutic agent, and wherein the therapeutic agent is housed in a cavity that is separate from the imageable solid marker element.

* * * * *